(12) United States Patent
Fleischer et al.

(10) Patent No.: US 7,772,617 B2
(45) Date of Patent: Aug. 10, 2010

(54) GAS SENSITIVE FIELD-EFFECT-TRANSISTOR

(75) Inventors: Maximilian Fleischer, Höhenkirchen (DE); Hans Meixner, Haar (DE); Uwe Lampe, Buxtehude (DE); Roland Pohle, Herdweg (DE); Ralf Schneider, München (DE); Elfriede Simon, München (DE)

(73) Assignee: Micronas GmbH, Freiburg (DE)

( * ) Notice: Subject to any disclaimer, the term of this patent is extended or adjusted under 35 U.S.C. 154(b) by 562 days.

(21) Appl. No.: 11/393,371

(22) Filed: Mar. 30, 2006

(65) Prior Publication Data

US 2006/0278528 A1    Dec. 14, 2006

(30) Foreign Application Priority Data

Mar. 31, 2005    (DE) .................. 10 2005 014 777

(51) Int. Cl.
   *G01N 27/414*    (2006.01)
(52) U.S. Cl. ....................................... 257/253
(58) Field of Classification Search .......... 257/253; 204/406; 324/769
   See application file for complete search history.

(56) References Cited

U.S. PATENT DOCUMENTS

| | | | |
|---|---|---|---|
| 3,663,870 A | 5/1972 | Tsutsumi et al. | |
| 4,023,549 A | 5/1977 | Hewitt | |
| 4,151,060 A | 4/1979 | Isenberg | |
| 4,354,308 A | 10/1982 | Shimada et al. | |
| 4,488,556 A * | 12/1984 | Ho ............................. | 600/348 |
| 4,633,704 A | 1/1987 | Tantram et al. | |
| 4,638,346 A | 1/1987 | Inami et al. | |
| 4,792,433 A | 12/1988 | Katsura et al. | |
| 5,635,628 A | 6/1997 | Fleischer et al. | |
| 5,879,527 A | 3/1999 | Kiesele et al. | |
| 6,041,643 A | 3/2000 | Stokes et al. | |
| 6,454,834 B1 | 9/2002 | Livingstone et al. | |
| 6,566,894 B2 | 5/2003 | Rump | |
| 6,935,158 B2 | 8/2005 | Serina et al. | |

(Continued)

FOREIGN PATENT DOCUMENTS

DE    2947050    11/1979

(Continued)

OTHER PUBLICATIONS

Pohle et al., "Realization of a new sensor concept: improved CCFET and SGFET type gas sensors in Hybrid Flip-Chip technology", 12th International Conference on Transducers, Solid-State Sensors, Actuators, and Microsystems (2003) vol. 1 pp. 135-138.*

(Continued)

*Primary Examiner*—Thomas L Dickey
(74) *Attorney, Agent, or Firm*—O'Shea Getz P.C.

(57) ABSTRACT

A gas sensitive field effect transistor comprises a semiconductor substrate that includes a capacitance well, and source and drain regions of a field effect transistor. A gate of the field effect transistor is separated from the semiconductor substrate by an insulator, and a gas sensitive layer separated from the gate by an air gap. The field effect transistor provides an output signal indicative of the presence of a target gas within the air gap to an amplifier, which provides an amplified output signal that is electrically coupled to the capacitance well.

5 Claims, 5 Drawing Sheets

U.S. PATENT DOCUMENTS

| | | | |
|---|---|---|---|
| 2002/0092974 A1 | 7/2002 | Kouznetsov | |
| 2004/0112764 A1 | 6/2004 | Stokes et al. | |
| 2004/0133116 A1 | 7/2004 | Abraham-Fuchs et al. | |
| 2005/0035808 A1 | 2/2005 | Frerichs | 19/175 |

FOREIGN PATENT DOCUMENTS

| | | | |
|---|---|---|---|
| DE | 4028062 | 9/1990 | |
| DE | 4105598 | 9/1992 | |
| DE | 4239319 | 4/1993 | |
| DE | 43 33 875 | 4/1995 | 27/414 |
| DE | 19534557 | 3/1997 | |
| DE | 19613274 | 10/1997 | |
| DE | 197 08 770 | 8/1998 | |
| DE | 10245947 | 4/2004 | |
| EP | 0952447 | 4/1998 | |
| EP | 0 947 829 | 10/1999 | 27/414 |
| EP | 1 059 528 | 5/2000 | |
| EP | 1103809 | 5/2001 | |
| EP | 1 176 418 | 1/2002 | 27/22 |
| EP | 1484605 A2 * | 12/2004 | |
| JP | 01059049 | 3/1989 | |
| JP | 03131749 | 6/1991 | |
| JP | 03259736 | 11/1991 | |
| WO | WO 94/23288 | 10/1994 | |
| WO | WO 96/01992 | 1/1996 | |
| WO | WO 98/41853 | 9/1998 | |
| WO | WO 03/050526 | 6/2003 | |

OTHER PUBLICATIONS

Gergintschew et al., "The capacitively controlled field effect transistor (CCFET) as a new low power gas sensor," Sensors and Actuators B, Elsevier, vol. 36, No. 1, 1996, pp. 285-289.

Pohle et al., "Realization of a New Sensor Concept: Improved CCFET and SGFET Type Gas Sensors in Hybrid Flip-Chip Technology," Transducers, 12$^{th}$ International Conference on Solid-State Sensors, Actuators and Microsystems, Jun. 2003, vol. 1, 9, pp. 135-138.

Kienle et al., "Acticated Charcoal and its Industrial Application," Stuttgart : Enke, ISBN 3-432-90881-4, pp. 126 and 162-163, 1980.

Müller et al., "Adsorber for a Low Solvent Load," Intelligent Exhaust Air Cleaning Using Electric Current, Verfahrenstechnik, vol. 37, No. 9, pp. 30-31, 2003.

CCI Charcoal International : Activated Charcoal Textiles Given Uniform Brand Name of Zorflex, MaschinenMarkt, 2004, No. 17, p. 89.

Leu et al., "Evaluation of gas mixtures with different sensitive layers incorporated in hybrid FET structures," Sensors and Actuators B, Elsevier Sequoia, vol. 18-19, 1994, pp. 678-681.

Wöllenstein et al., "Cobalt oxide based gas sensors on silicon substrate for operation at low temperatures," Sensors and Actuators B: Chemical, Elsevier Sequoia, vol. 93, No. 1-3, Aug. 2003, pp. 442-448.

Fleischer et al., "Selective gas detection with high-temperature operated metal oxides using catalytic filters," Sensors and Actuators B, vol. 69, pp. 205-210, 2000.

Peschke et al., "Optimization of Sputtered SnO2 Films as Gas-sensitive Layers for Suspended-gate FETs", Sensors and Actuators B, 1991, pp. 157-160, XP-002379749.

Lampe et al., "GasFET for the detection of reducing gases", Sensors and Actuators B 111-112, 2005, pp. 106-110.

Mizsei et al., "Simultaneous Response of Work Function and Resistivity of some SnO2-based Samples to H2 and H2S", Sensors and Actuators B, 4 (1991), pp. 163-168, XP-002379750.

Doll et al., "Gas detection with work function sensors", Proceedings of the SPIE, SPIE, Bellingham, VA, US, vol. 3539, Nov. 1998, pp. 96-105, XP-002329891.

Paris et al., "57.5: Low Drift Air-Gap CMOS-FET Gas Sensor," Proceedings of IEEE Sensors, vol. 1 of 2, Conf. 1, Jun. 12, 2002, pp. 421-425, 2002, XP010605129, ISBN: 0-7803-7454-1.

Burgmair et al., "Humidity and temperature compensation in work function gas sensor FETs," Sensors and Actuators B, Elsevier Sequoia S.A., Lausanne, CH, vol. 93, No. 1-3, pp. 271-275, 2003.

Burgmair et al., "Field effect transducers for work function gas measurements : device improvements and comparison of performance," Sensors and Actuators B, Elsevier Sequoia S.A., Lausanne, CH, vol. 95, No. 1-3, pp. 183-188, 2003.

Covington, et al. "Combined smart chemFET/resistive sensor array," Proceedings of the IEEE, vol. 2., pp. 1120-1123, 2003.

Doll et al., "Modular System Composed of Hybrid GasFET Modules," ITG-Technical Report 126: Sensors-Technology and Application, VDE Verlag, Berlin, Germany, 1994, pp. 465-470, XP-000874734.

M. Lehmann, "Nanometre Dimensions in Bio and Gas Sensor Technology", MST News, Mar. 2004, pp. 43-47, XP-002379751.

* cited by examiner

GAS SENSITIVE FIELD-EFFECT-TRANSISTOR

PRIORITY INFORMATION

This patent application claims priority from German patent application 10 2005 014 777.1 filed Apr. 1, 2005, which is hereby incorporated by reference.

BACKGROUND OF THE INVENTION

The present invention relates to the field of semiconductor sensors, and in particular to a semiconductive sensor with a gas sensitive field effect transistor.

Gas sensors that utilize the change in work function of sensitive materials as the physical parameter have a fundamental development potential. The reasons for this relate to their advantages which are reflected in their low operating power, inexpensive fabrication and design technology, as well as the wide range of target gases. The latter can be detected with this platform technology since numerous different detection substances can be integrated in these designs.

FIG. 5 illustrates the sensor design based on the principle of a so-called suspended-gate field-effect transistor (SGFET). The bottom of the gate electrode, which is raised in this design, has the sensitive layer on which an electrical potential is generated in response to the presence of the gas to be detected based on absorption, which potential corresponds to a change in the work function of the sensitive material. As a rule, the signals have a level between 50 and 100 mV. This potential acts on the channel of the FET structure, thereby changing the current between the source and the drain ($I_{DS}$). The coupling of this potential to the source-drain current is as a function of the gate capacitance C and of the ratios of channel width to channel length W/L:

$$I_{DS} \propto \frac{W}{L} \cdot c \quad [1]$$

(c: area-specific gate capacitance in $F/m^2$)

The changed source-drain current is read out directly. Alternatively, the change in the source-drain current is reset by applying an additional voltage to the raised gate or to the transistor well. The additional voltage required represents the readout signal which is directly correlated with the work function change in the sensitive layer.

The SGFET has limitations in regard to the attainable signal quality due to the geometry required by the dimensioning of the FET structure. The available surface for coupling is limited by the process-technology-determined parameter W/L. Also related to the above factors, the signal quality is significantly affected by the introduction of the air gap between the gate and channel regions and the concomitant reduction of the gate capacitance. The height of the air gap must allow for sufficiently rapid diffusion of the gas and is in the range of a few p.m.

Use of the CCFET (capacitively controlled FET) design shown in FIG. 6 largely eliminates the limitations associated with the SGFET by providing a more flexible dimensionability. As a result, significant optimization is enabled in regard to signal quality. In the CCFET, the readout transistor 5, shown as source S and drain D, is controlled by a noncontacted gate (floating gate). Together with the opposing gate electrode which has the gas-sensitive layer, the noncontacted gate forms a capacitor arrangement. The surface of the capacitor arrangement is independent of the readout transistor and can thus be enlarged, thereby producing improved signal coupling.

However, the fact that parasitic capacitances are present between the floating gate 2 and the substrate or capacitance well 3 does have a disadvantageous effect even with the CCFET.

If the direct capacitances present in a gas-sensitive field-effect transistor are shown graphically in equivalent circuits, the diagrams of FIGS. 7 and 8 can be drawn up for the SGFET and CCFET variants. In FIG. 7, the SGFET clearly has a structure which is composed of a series connection of individual capacitances of air gap $C_L$ and those of the readout transistor $C_G$.

$$C_{SGFET} = C_L \cdot C_G / (C_L + C_G)$$

For a given sensitive layer and a given transistor, the air gap height is thus the single variable. In this case, no improvement of the signal coupling is possible by using an appropriate electrical control. A CCFET structure, for which a capacitive functional diagram is illustrated in FIG. 6, contains an additional electrode, the so-called capacitance well 3 located below the floating gate 2. As a result, the potential at the floating gate is determined by an expanded capacitive voltage divider which is formed from the air gap capacitance $C_L$, the capacitance of the gate $C_G$, and the capacitance occurring between the floating gate and that due to the capacitance well, as illustrated in FIG. 8. By enlarging the area forming capacitance $C_L$, it is possible to reduce the effect of the parasitic gate capacitance while maintaining the air gap height. The gate capacitance of the readout transistor is—especially given appropriate dimensioning—negligible with good approximation relative to other capacitances. The capacitance well is used to shield the floating gate electrode and is accordingly connected to ground. Assuming the above preconditions, the potential at the floating gate $U_{UF}$ is:

$$\Delta U_{FG} = \Delta \Phi_S \cdot C_L \cdot (C_L + C_W + C_G)/(C_G + C_W) \quad [2]$$

The changes in the $U_{FG}$ are converted through the transistor characteristic directly into changes in the source-drain current $I_{DS}$ and in response to a given $\Delta \Phi_s$ are a direct measure of the signal obtained with the gas sensor. Based on the introduction of an air gap with a height of a few μm, the result is:

$$C_L << C_G + C_W \quad [3]$$

The result up to this point is a significant loss of signal.

The two variants according to the equivalent circuits of FIGS. 7 and 8 function by coupling the gas signal to the source-drain current $I_{DS}$, used as an example of the measured quantity. The signal is degraded, however, due to the capacitances present. With the SGFET, this factor can be counteracted by increasing the W/L, and additionally in the CCFET by increasing the surface of the readout capacitance, such that in the limiting case a very large area is obtained whereby $C_G << C_W$.

$$\Delta U_{FG} \propto \Delta \Phi_S \cdot C_L / C_W \quad [4]$$

Using parameters possible in a standard CMOS process, in the CCFET a weakening of the signal on the order of 1:10 to 1:100 caused by the capacitive voltage divider must be expected with the operating method described above.

There is a need for an improved gas-sensitive field-effect transistor which largely eliminates interference effects.

SUMMARY OF THE INVENTION

The invention is based on the knowledge that the circuitry of a CCFET in which a reference electrode/capacitance well is provided must be implemented, when reading out the work function change in gas-sensitive layers, such that by using appropriate switching measures, such as tracking the potentials of certain electrodes, parasitic effects of capacitances contained in the design can be reduced. This has a direct effect on the coupling of the signal of the gas-sensitive layer to the current $I_{DRAIN/SOURCE}$, and thus effects an amplification of the signal of the gas sensor by one to two orders of magnitude.

The effect of adapting or tracking the noncontacting floating gate electrode and the reference electrode to the same potential is that parasitic capacitances, such as, for example, capacitance $C_W$ between the floating gate electrode and the reference electrode no longer have any effect, so that ideally the following situation results based on equation [2]:

$$\Delta U_{FG} = \Delta \Phi_S \cdot C_L/(C_G) \quad [5] \quad >> \quad \Delta \Phi_S \cdot C_L/(C_G + C_W) \quad \text{in analogy to [2]}$$
$$>> \quad \Delta \Phi_S \cdot C_L/(C_W) \quad \text{in analogy to [4]}$$

These and other objects, features and advantages of the present invention will become more apparent in light of the following detailed description of preferred embodiments thereof, as illustrated in the accompanying drawings.

DETAILED DESCRIPTION OF THE INVENTION

Figure 6:
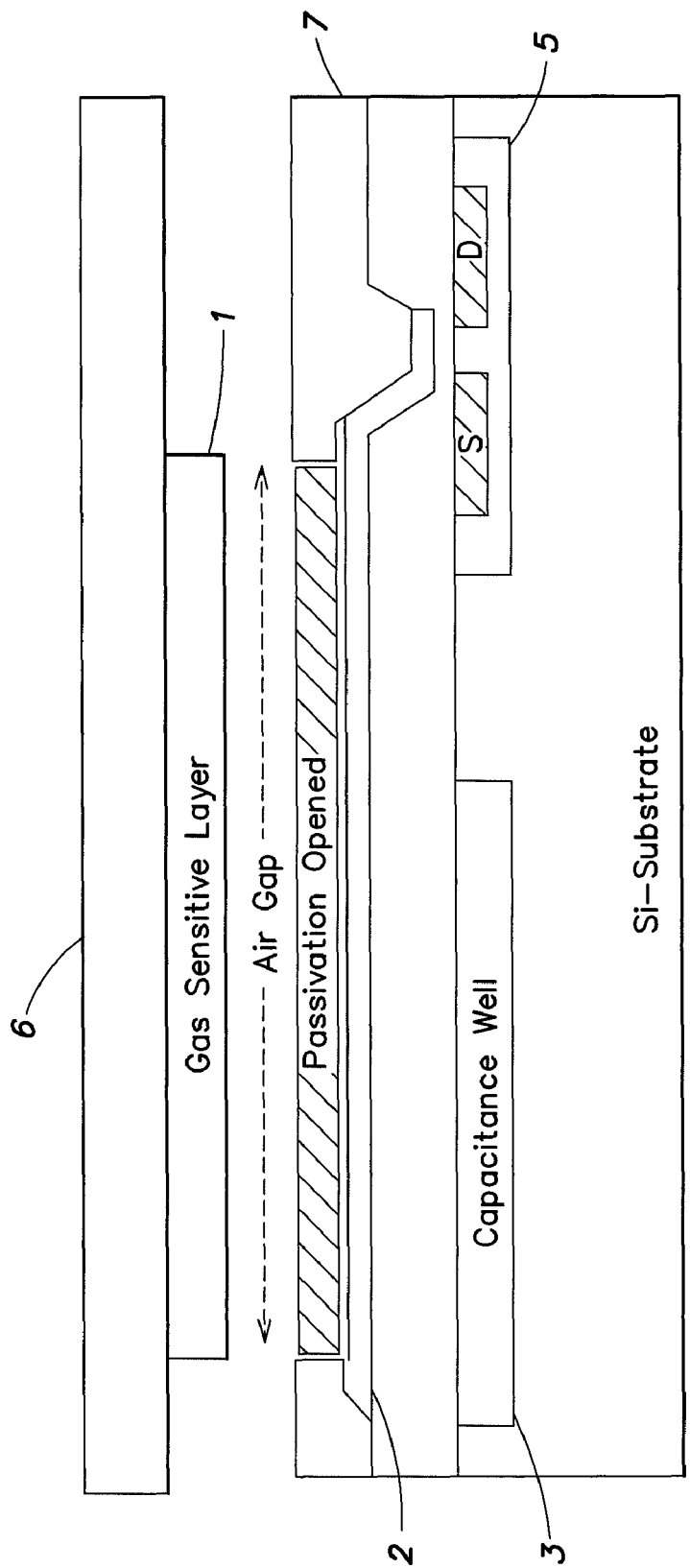

In a CCFET structure, for example that of FIG. 6, an appropriate reference electrode, generally called a capacitance well, is contained in the structure. This electrode is located below noncontacting floating gate electrode 2. As a result, the potential at the floating gate is determined by an extended capacitive voltage divider which is formed from the air gap capacitance $C_L$, the capacitance of the gate or gate electrode 6, and the capacitance occurring between the floating gate electrode 2 and the reference electrode 3. The reference electrode 3 defines the potential of floating gate electrode 2, which action occurs as a result of the difference between the potentials of the gate electrode and the reference electrode. A change in the potential at the reference electrode/FG results as defined by equation [2].

Figure 1:
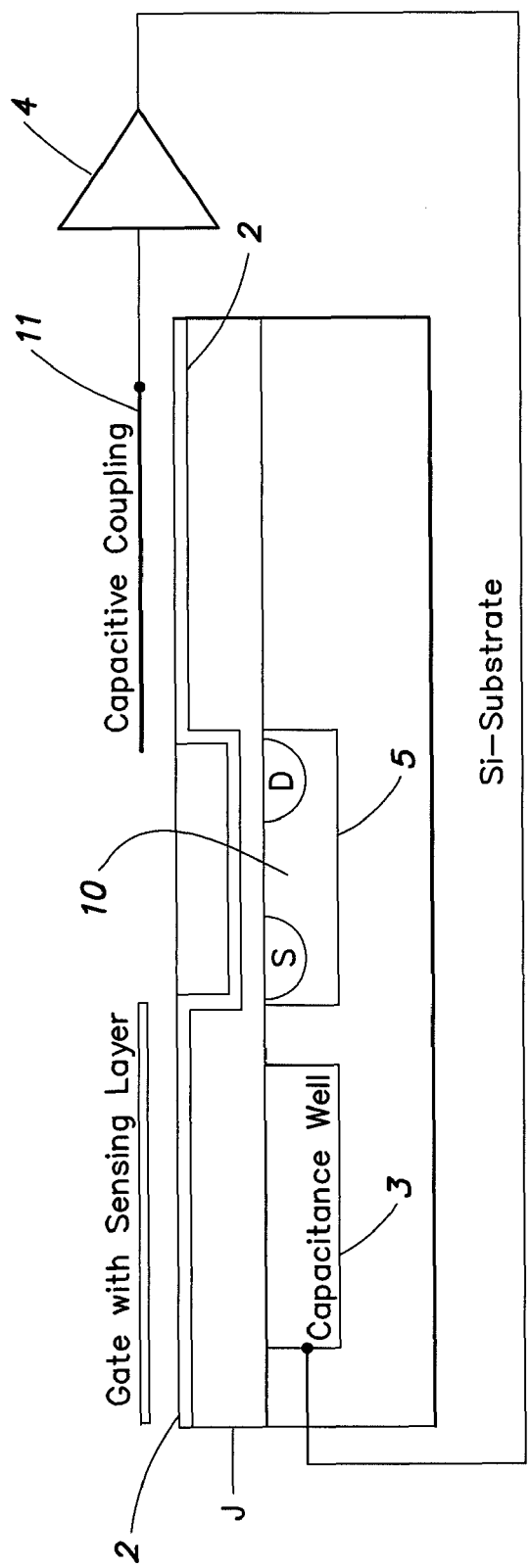
FIG. 1 shows an embodiment of a CCFET with capacitive coupling to floating gate 2.
Figure 2:
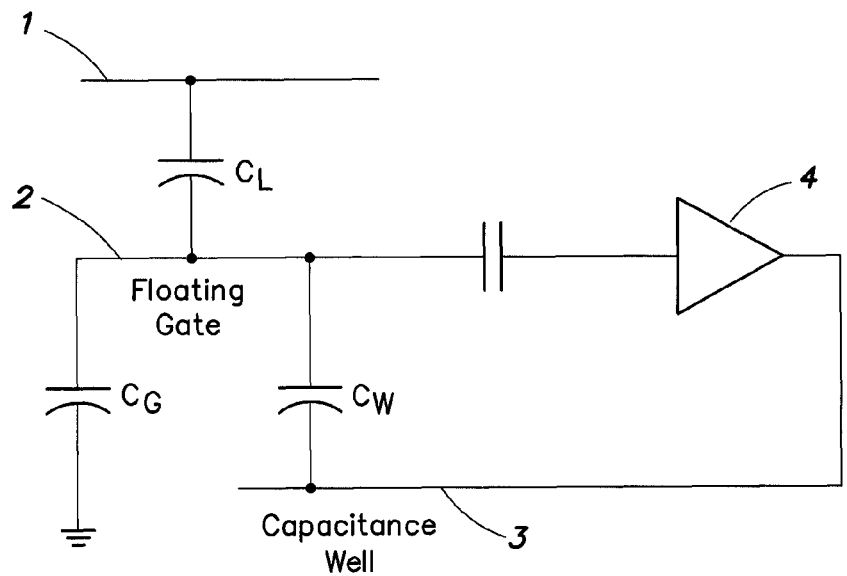
FIG. 2 is a schematic diagram illustrating the tracking of reference electrode/capacitance well 3 when used, capacitively decoupled, amplified, and for tracking the reference electrode.
Figure 3:
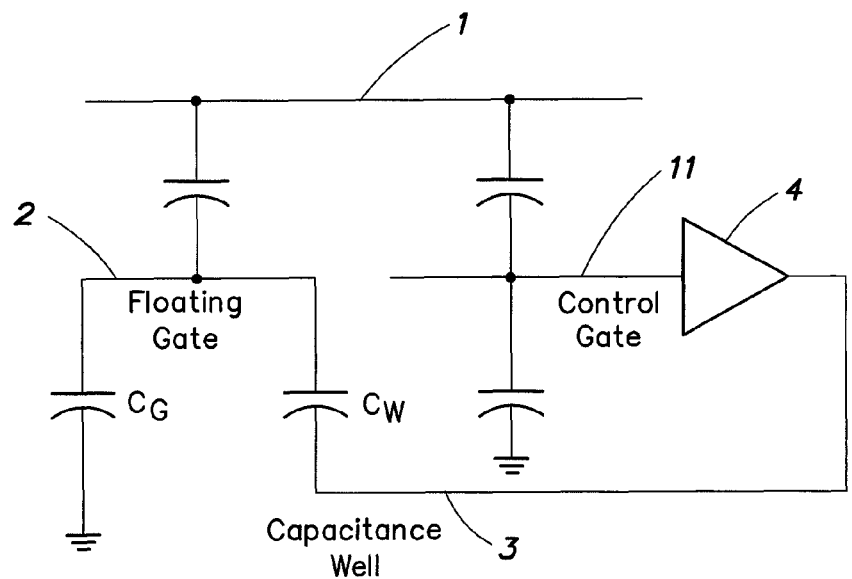
FIG. 3 is a schematic diagram illustrating tracking of a reference electrode, wherein a signal potential-correlated with the floating gate can be generated through an additional electrode, in particular, in the air gap.
Figure 4:
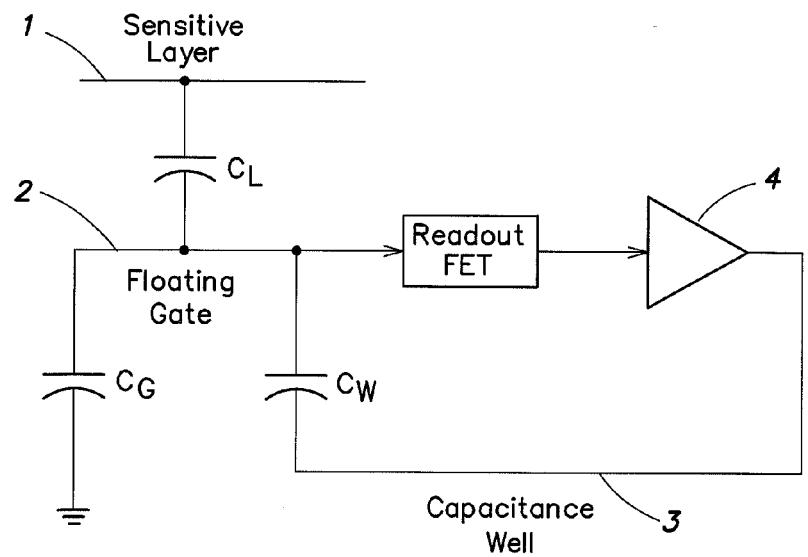
FIG. 4 is a schematic diagram illustrating the tracking of the reference electrode through the output signal of the readout transistor.
Figure 5:
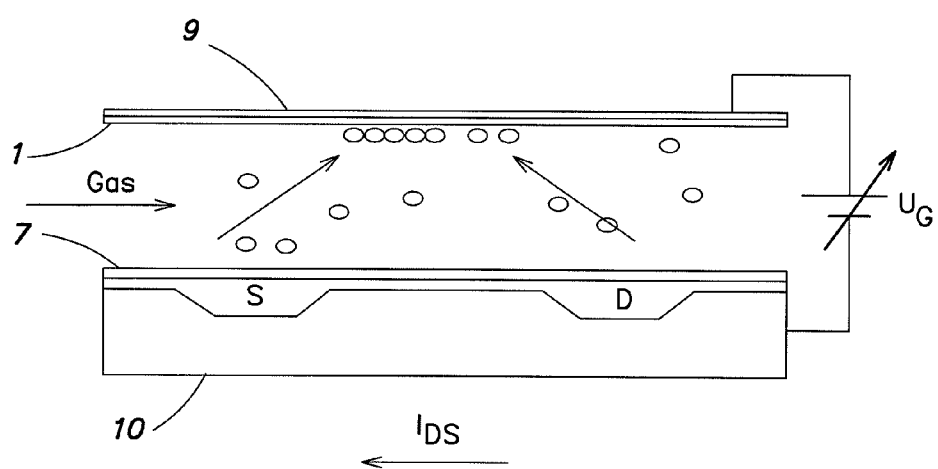
FIGS. 5 and 6 are schematic diagrams showing the design of a gas-sensitive field-effect transistor, a CCFET being illustrated in FIG. 6.
Figure 8:
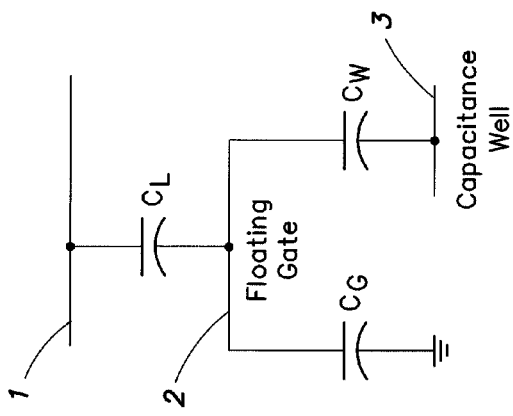
FIGS. 7 and 8 are equivalent circuit diagrams for FIG. 5 or 6.
Figure 7:
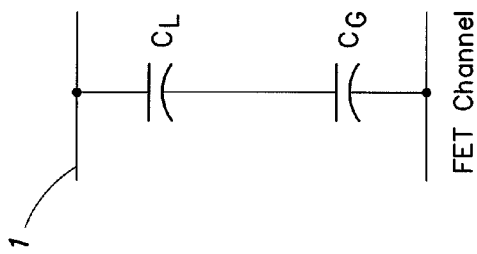

FIG. 7 illustrates an equivalent circuit diagram of an SGFET and FIG. 8 illustrates an equivalent circuit diagram of a CCFET, FIGS. 2, 3 and 4, as well as FIG. 1, illustrate variants of the invention. It is evident from the prior art reproduced in FIGS. 5 through 7 that, according to FIGS. 5 and 7, no additional parasitic effects influenceable by additional electrodes are produced between the gas-sensitive layer 1 and the channel of the field-effect transistor. Only the capacitances of air gap $C_L$ and gate $C_G$ are present. Based on the diagrams for a CCFET in FIGS. 6 and 8, it is evident that additional capacitance is present in the design due to the reference electrode/capacitance well 3, which capacitance may under certain circumstances have parasitic effects. Capacitance $C_w$ is formed between the floating gate 2 and the reference electrode 3.

Due to the tracking of the potential of the reference electrode 3, the parasitic effect of capacitance $C_w$, and under certain circumstances the effect of the substrate as well, which is generally composed of silicon, are eliminated. The result is an improvement in the coupling of the gas signal to the channel region of the transistor, and thus a gain in the gas sensor signal by several orders of magnitude.

The three possible variants for implementing the method according to the invention are shown in FIGS. 2, 3, and 4, as well as in FIG. 1. Fundamentally, the potential of the reference electrode/floating gate electrode 2 is decoupled and utilized in electrically decoupled form in order to control reference electrode/capacitance well 3. As a result, losses due to parasitic capacitances are compensated, wherein an intermediate gain by an amplifier 4, which in particular has a high input resistance and thus functions as an isolation amplifier, and a corresponding switching circuit are controlled. The goal is the tracking of the potential of the reference electrode to the potential of the noncontacting floating gate electrode.

According to equation [5], the tracking of the voltage $U_w$ at the reference electrode 3 can be effected whereby the potential $U_{FG}$ at the floating gate electrode 2 is capacitatively decoupled, then applied in electrically decoupled form to the reference electrode.

This decoupling of potential $U_{FG}$ can be effected capacitively directly from the floating gate electrode 2. Alternatively, an additional electrode, for example, one incorporated in the air gap, can serve as the control electrode, wherein the differences between potentials $U_{FG}$ and $U_w$ are compensated through the gain of the circuit. As a result, the dimensioning of the control electrode 11 is not strongly tied to the design of the floating gate electrode.

FIG. 4 shows another approach to achieving the tracking of the potential $U_w$ within the gas-sensitive field-effect transistor. For this purpose, the reference electrode 3 is reached through the amplified output signal of the sensor or of the readout transistor. The potential of the floating gate electrode 2 is connected directly to the readout transistor, and the output signal thereof is in turn connected to the amplifier 4. The amplified signal is supplied to the reference electrode 3.

The advantages of the invention provide overall high signal qualities from the gas-sensitive field-effect transistors, wherein interference effects such as signal drift or noise are suppressed due to improved coupling of the work function generated at the gas-sensitive layer to the transistor current employed as the measured quantity. In addition, the increase in the amplitude of the measurement signal brings about a significant improvement in the signal-to-noise ratio. Due to the improved sensor signals, the required evaluation electronics can be designed in a more cost-effective manner.

FIG. 1 shows one possible variant of an embodiment with capacitive coupling to the floating gate electrode. The signal of the control electrode 11 is applied to the amplifier 4, the output signal of which in turn can be supplied to the reference electrode 3.

Figure 9:
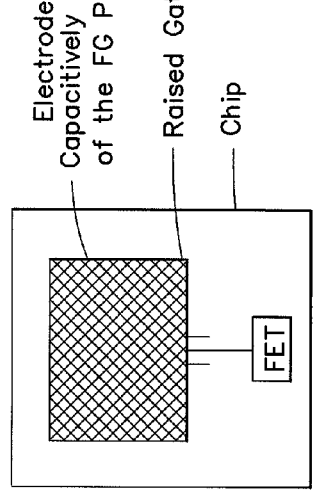
FIG. 9 shows an embodiment of the invention for decoupling the potential of the floating gate electrode, in this case implemented by an annular electrode surrounding the floating gate.

As indicated in FIG. 9, the decoupling of the potential from the floating gate electrode can be implemented by an annular electrode entirely surrounding the floating gate. FIG. 9 provides a top view of a chip, wherein a field-effect transistor is mounted to effect the readout, along with a raised gate, and an electrode for capacitively tapping the potential at the centrally positioned floating gate.

The electronics required for the elimination of the parasitic components can be advantageously integrated as an integrated circuit into the Si chip which contains the FET structure.

Although the present invention has been illustrated and described with respect to several preferred embodiments thereof, various changes, omissions and additions to the form and detail thereof, may be made therein, without departing from the spirit and scope of the invention.

What is claimed is:

1. A gas-sensitive field-effect transistor (FET) comprising:
    a semiconductor substrate;
    a gate electrode that includes a gas-sensitive layer;
    an air gap between the gas-sensitive layer and the semiconductor substrate;
    a noncontacting floating gate electrode that is capacitively coupled to the gate electrode;
    a field-effect transistor that includes the floating gate electrode, a source and a drain, and provides a sensed signal indicative of the electrical potential on the floating gate electrode;
    an amplifier that receives the sensed signal and that provides an amplified sensed signal; and
    a reference electrode, which together with the floating gate electrode forms a capacitance $C_W$, and that is electrically coupled to the amplified sensed signal.

2. The gas-sensitive field-effect transistor (FET) of claim 1, where an electronic circuit to reduce parasitic components is integrated into the semiconductor substrate.

3. The gas-sensitive field-effect transistor (FET) of claim 2, where in order to read out the potential of the floating gate electrode, a control electrode in coupling connection with the floating gate electrode is provided, the potential decoupled from the floating gate electrode can be supplied to the amplifier, and the amplified sensed signal is applied to the reference electrode in order to control the latter.

4. A gas-sensitive field effect transistor, comprising:
    a semiconductor substrate that includes a capacitance well, and source and drain regions of a field effect transistor;
    a gate of the field effect transistor separated from the semiconductor substrate by an insulator;
    a gas sensitive layer separated from the gate by an air gap;
    an amplifier that receives an output signal from the field effect transistor and provides an amplified output signal that is electrically coupled to the capacitance well;
    where the output signal is indicative of the presence of a target gas within the air gap.

5. The gas sensitive field effect transistor of claim 4, where the substrate is a silicon substrate.

\* \* \* \* \*